US007091312B2

(12) United States Patent
Chen et al.

(10) Patent No.: US 7,091,312 B2
(45) Date of Patent: Aug. 15, 2006

(54) BIOCIDAL PROTEIN

(75) Inventors: Ching-San Chen, Taipei (TW); Kuan-Chung Chen, Changhua (TW); Cheng-Chun Kuan, Taipei (TW); Ching-Yu Lin, I-Lan (TW)

(73) Assignee: Academia Sinica, Taipei (TW)

( * ) Notice: Subject to any disclaimer, the term of this patent is extended or adjusted under 35 U.S.C. 154(b) by 275 days.

(21) Appl. No.: 10/409,818

(22) Filed: Apr. 8, 2003

(65) Prior Publication Data

US 2004/0005682 A1 Jan. 8, 2004

Related U.S. Application Data

(62) Division of application No. 09/686,332, filed on Oct. 11, 2000, now Pat. No. 6,653,463.

(51) Int. Cl.
  *C07K 14/415* (2006.01)
  *A01N 37/18* (2006.01)
(52) U.S. Cl. .................. 530/324; 530/300; 530/370; 530/372; 530/377; 530/379; 514/12; 435/69.1
(58) Field of Classification Search ................ 530/324, 530/300, 370, 372, 377, 379; 435/69.1; 514/12
See application file for complete search history.

(56) References Cited

OTHER PUBLICATIONS

Osborn et al. Isolation and characterisation of plant defensins from seeds of Asteraceae, Fabaceae, Hippocastanaceae and Saxifragaceae. 1995. FEBS letters 368 (2) p. 257-62.*
Garcia-Olmedo et al. Plant defense peptides. 1998. Biopolymers 47 (6) p. 479-91.*
Eppel et al.Overexpression of an endogenous thionin enhances resistance of Arabidopsis against Fusarium oxysporum. 1997. Plant Cell 9 (4) p. 509-20.*
Thomma et al. Plant defensins. 2002. Planta 216 (2): p. 193-202.*
Bloch et al., "A New Family of Small (5 kDa) Protein Inhibitors of Insect α-amylases From Seeds or Sorghum (Sorghum bicolor (L) Moench) Have Sequence Homologies With Wheat γ-Purothionins", , FEBS Letters, vol. 279, No. 1, pp. 101-104 (1991).
Carlini et al., "Biological Effects of Canatoxin in Different Insect Models: Evidence for A Proteolytic Activation of the Toxin by Insect Cathepsinlike Enzymes", J. Econ Entomol 90: 340-348 (1997).
Ferreira et al., "Proteolytic Activation of Canatoxin, a Plant Toxic Protein, by Insect Cathepsin-Like Enzyme," Arch Insect Biochem Physiol 44: 162-171 (2000).
Froy et al., "Membrane Potential Modulators: A Thread of Scarlet From Plants to Humans," The FASEB Journal, vol. 12, No. 15, pp. 1793-1796 (1998).
Ghazaleh et al., "Stimulation of Calcium Influx and Platelet Activation by Canatoxin: Methoxyverapamil Inhibition and Downregulation by cGMP," Arch Biochem Biophys 339: 362-367 (1997).
Hilder et al., "Protein and cDNA Sequences of Bowman-Birk Protease Inhibitors From the Cowpea (Vigna unguiculata Walp.)", Plant Molecular Biology, vol. 13, No. 6, pp. 701-710 (1989).

Ishimoto et al., "Protective Mechanism of the Mexican Bean Weevil Against High Levels of Alpha-Amylase Inhibitor in the Common Bean," Plant Physiol 111: 393-401 (1996).
Ishimoto et al., "Insecticidal Activity of an α-amylase Inhibitor-like Protein Resembling a Putative Precursor of α-amylase Inhibitor in the Common Bean, Phaseolus Vulgaris L," Biochemica Biophysica Acta, pp. 104-112 (1999).
Janzen et al "Insecticidal Action of the Phytohemagglutinin in Black Beans on a Bruchid Beetle," Science 192: 795-796 (1976).
Kaga et al., "Genetic Localization of a Bruchid Resistance Gene and Its Relationship to Insecticidal Cyclopeptide Alkaloids, the Vignatic Acids, in Mungbean (Vigna Radiata L. Wilczek)," Molecular & General Genetics, vol. 258, No. 3, pp. 378-384 (1998).
Koiwa et al., "Phage Display Selection Can Differentiate Insecticidal Activity of Soybean Cystatins Plan" J 14: 371-379 (1998).
Kornegay et al., "Inheritance of resistant to Mexican Bean Weevilin Common Bean, Determined by Bioassay and Biochemical Tests," Crop Sci 33: 589-594 (1993).
Macedo et al., "Purification and Properties of Storage Proteins (vicilins) from Cowpea (*Vigna unguiculata*) Seeds Which are Susceptible or Resistant to the Bruchid Beetle *Callosobruchus maculates*," Brazilian Journal of Medical and Biological Research, vol. 28(2), pp. 183-190 (1995).
Modgil R. Mehta, "Effect of *Callosobruchus Chinensis* (Bruchid) Infestation on Antinutritional Factors in Stored Legumes," Plant Foods Hum Nutr 50: 317-323 (1997).
Moraes et al., "Lima bean (*Phaseolus lunatus*) Seed Coat Phaseolin is Detrimental to the Cowpea Weevil (*Callosobruchus maculatus*)," Braz J Med Biol Res. 33: 191-198 (2000).
Osborn et al., "Insecticidal Activity And Lectin Homology of Arcelin Seed Protein," Science 240: 207-210 (1988).
Pusztai et al., "Nutritional Evaluation of the Tryspin (EC 3.4.21.4) Inhibitor From Cowpea (Vigna Unguiculata Walp.)," The British Journal of Nutrition, vol. 68, No. 3, pp. 783-791 (1992).
Sugawara et al., "Insecticidal Peptide From Mungbean: A Resistant Factor Against Infestation with Azuki Bean Weevil," Journal of Agricultural and Food Chemistry, vol. 44, No. 10, pp. 3360-3364 (1996).
Suzuki et al., "cDNA Sequence and Deduced Primary Structure of an α-amylase Inhibitor from a Bruchid-Resistant Wild Common Bean," Biochemica Biophysica Acta, vol. 1206, No. 2, pp. 289-291 (1994).
Zhang et al., "Fabatins: New Antimicrobial Plant Peptides," FEMS Microbiology Letters, vol. 149, pp. 59-64 (1997).

(Continued)

*Primary Examiner*—Gabriele Bugaisky
(74) *Attorney, Agent, or Firm*—Fish & Richardson P.C.

(57) ABSTRACT

The invention relates to novel nucleic acid and protein sequences from the mung bean *Vigna radiata*. The nucleic acid sequence, isolated from a bruchid resistant mung bean line, encodes a thionin-like protein with insecticidal properties.

9 Claims, No Drawings

OTHER PUBLICATIONS

Zhu et al., "An Insecticidal N-Acetylglucosamine-Specific Lectin Gene From Griffonia Simplicifolia," (Leguminosae). *Plant Physiol* 110: 195-202 (1996).

Zhu-Salzman et al., "Carbohydrate Binding and Resistance to Proteolysis Control Insecticidal Activity of Griffonia Simplicifolia Lectin II," *Proc Natl Acad Sci U S A* 95: 15123-15128 (1998).

Masao et al., "Biochemical and Genetic Basis of the Insect Resistance in Mungbean," *Abstract Book of the 6th International Congress of Plant Molecular Biology* (Jun. 2000).

Masayashi et al., Genomic Information of the Bruchid Resistance Locus, Br, In Mungbean, *Abstract Book of the 6th International Congress of Plant Molecular Biology* (Jun. 2000).

* cited by examiner

BIOCIDAL PROTEIN

RELATED APPLICATIONS

This application is a divisional application and claims priority to U.S. application Ser. No. 09/686,332, filed Oct. 11, 2000 now U.S. Pat. No. 6,653,463, the contents of which are incorporated herein by reference.

BACKGROUND OF THE INVENTION

Advances in biotechnology have enabled the generation of plants which express recombinant proteins. Thus, plants can be engineered to overproduce a variety of polypeptides with desirable qualities. Such polypeptide can include enzymes which produce secondary metabolites, proteins with medicinal or pharmaceutical properties, and proteins which endow the plants with new traits, for example, resistance to diseases, pathogens, and environmental conditions.

Given the vulnerability of agricultural crops to damage by insects, and other pests and pathogens, the ability to provide additional protective means and agents is of considerable importance. Moreover, traditional breeding techniques have identified plant lines with Mendelian traits endowing resistance to pests and pathogens. Modern molecular biological techniques can now be applied to isolate the critical nucleic acids and proteins with these properties in order to enhance the resistance of more sensitive plants or to antagonize the pests and pathogens in a variety of scenarios.

SUMMARY OF THE INVENTION

The invention is based, in part, on the discovery of a novel mung bean nucleic acid which is expressed in a mung bean plant line that is resistant to insect attack, but not expressed in sensitive plant lines. The nucleic acid encodes a polypeptide which has insecticidal activity and which has similarity to thionin proteins. The sequence of the mung bean thionin nucleic acid (SEQ ID NO:1), designated as "VrCRP", is shown below:

5'-ACCTCAACAATTCATCACTC<u>ATG</u>GAGAGAAAAACTTTCAGCTTCTTG

TTCTCGCTCCTTCTCGTCTTAGCCTCTGATGTGGCCGTAGAGAGAGGAGA

GGCTAGAACTTGTATGATAAAGAAGAAGGGTGGGAAAATGCTTAATTG

ACACCACCTGTGCACATTCGTGCAAGAACCGCGGTTACATAGGTGGAGAT

TGCAAAGGCATGACGCGCACCTGCTATTGCCTCGTCAACTGT<u>TGA</u>ACCCT

TTTCGAATATCATATCATCTTATCACAAATAAATATAGCAGCATCACTGC

TACTAGTACCGCCCTCCGCACCACGCCCT-3'

The initiator and terminator codons are underlined and in boldface. The sequence of the mung bean thionin polypeptide sequence (SEQ ID NO:2), designated as "VrCRP", is shown below:

MERKTFSFLFSLLLVLASDVAVERGEARTCMIKKEGWGKCLIDTTCAHSC
KNRGYIGGDCKGMTRTCYCLVNC

The invention is also based on the discovery the a polypeptide derived from VrCRP which has the VrCRP signal sequence removed is biologically active as an insecticide and fungicide. This polypeptide is encoded by the nucleic acid sequence (SEQ ID NO:3) below:

GAGAGAGGAGAGGCTAGAACTTGTATGATAAAGAAAGAAGGGTGGGAAA

ATGCTTAATTGACACCACCTGTGCACATTCGTGCAAGAACCGCGGTTACA

TAGGTGGAGATTGCAAAGGCATGACGCGCACCTGCTATTGCCTCGTCAAC

TGTTGA

The polypeptide sequence (SEQ ID NO:4) of this form of VrCRP lacking the signal sequence is shown below:

ERGEARTCMIKKEGWGKCLIDTTCAHSCKNRGYIGGDCKGMTRTCYCLV
NC

Accordingly, in one aspect, the invention features isolated nucleic acid sequences which include a nucleic acid sequence comprising the nucleotide sequence of SEQ ID NO:1. The nucleic acids of the invention can further include nucleic acids which hybridize under stringent conditions to SEQ ID NO:1, as well as nucleic acids which are at least 50% identical, e.g., at least 60%, 70%, 80%, 90%, or 95% identical, to SEQ ID NO:1. Such nucleic acid sequences can encode a polypeptide which inhibits translation of messenger RNAs in a wheat germ extract, a polypeptide which has insecticidal activity, e.g., insecticidal activity against bruchids such as *Callosobruchus chinensis, Callosobruchus maculates*, and *Zabrotes subfasciatu*, or a polypeptide which has anti-fungal activity, e.g., against *Rhizoctonia solani*.

In another aspect, the invention features polypeptides comprising the amino acid sequence of SEQ ID NO:2. Featured polypeptides also include polypeptides which are at least 50% identical, e.g., at least 60%, 70%, 80%, 90%, or 95% identical, to SEQ ID NO:2. Such polypeptides can have at least one, two, three, four, five, eight, ten, twelve, or twenty conservative amino acids substitutions. The polypeptides can inhibit translation of messenger RNAs in a wheat germ extract, can have insecticidal activity, e.g., insecticidal activity against bruchids such as *Callosobruchus chinensis, Callosobruchus maculates*, and *Zabrotes subfasciatus*, or can have anti-fungal activity, e.g., against *Rhizoctonia solani*. Also encompassed by the invention are nucleic acid sequences encoding such polypeptides.

The featured polypeptides can be recombinant and/or purified. For example, they can be overexpressed in a variety of host cells, such as *E. coli*, Sf9 insect cells, plant cells and mammalian tissue culture cells using overexpression vectors known in the art. Lysates are made from the host cells, e.g., after overexpression is induced if induction is required. The polypeptides are purified from the lysate. Alternatively, the polypeptides are secreted, by the inclusion nucleic acid sequences encoding the signal peptide or a heterologous signal peptide. In another example, the featured polypeptides are encoded by a transgene and overproduced in a plant or a plant tissue. The plant is harvested and the polypeptides purified from the plant.

The purified and/or recombinant polypeptides can be formulated a composition. The composition can include an agriculturally acceptable carrier, e.g., one described below. The composition can contain the polypeptide at a concentration of about 0.005% to 10%, or about 0.01% to 1%, or about 0.1% to 0.5% by weight of composition. The composition can further include a cyclopeptide alkaloid, e.g., vignatic acid A and vignatic acid B, e.g., a cyclopeptide alkaloid with insecticidal properties. The composition can also include other desirable compounds, e.g., protease inhibitors, endotoxins, and the like. The contemplated compositions can have insecticidal activity, e.g., against bruchids such as *Callosobruchus chinensis, Callosobruchus maculates*, and *Zabrotes subfasciatu*, and/or anti-fungal activity, e.g., against *Rhizoctonia solani*. The compositions can be applied to plants and their environs by methods described below.

The nucleic acids of the invention can also include a heterologous promoter such that the promoter is operably linked to a coding genomic nucleic acid or a cDNA. The promoter can direct transcription of the nucleic acid in wounded or pathogen infected cells. The promoter can be induced by a signalling molecule, e.g., methyl jasmonate, salicylic acid, ethylene, absiscic acid, gibberillins, $HgCl_2$, and $H_2O_2$. The invention also features transformed cells which contain such nucleic acids, i.e., an aforementioned nucleic acid operably linked to a heterologous promoter. Also included are transgenic plants whose genomic DNA includes such nucleic acids, as are transgenic seeds from such plants.

A "purified polypeptide", as used herein, refers to a polypeptide that has been separated from other proteins, lipids, and nucleic acids with which it is naturally associated. The polypeptide can constitutes at least 10, 20, 50 70, 80 or 95% by dry weight of the purified preparation.

An "isolated nucleic acid" is a nucleic acid the structure of which is not identical to that of any naturally occurring nucleic acid, or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The "percent identity" of two amino acid sequences or of two nucleic acids is determined using the algorithm of Karlin and Altschul *Proc. Natl. Acad. Sci. USA* 87:2264–68, 1990, modified as in Karlin and Altschul *Proc. Natl. Acad. Sci. USA* 90:5873–77, 1993. Such an algorithm is incorporated into the NBLAST and XBLAST programs (version 2.0) of Altschul, et al. *J. Mol. Biol.* 215:403–10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17): 3389–3402, 1997. When utilizing BLAST and Gapped BLAST programs, the default parameters of the respective programs (e.g., XBLAST and NBLAST) can be used.

As used herein, the term "transgene" means a nucleic acid sequence (encoding, e.g., one or more subject thionin polypeptides), which is partly or entirely heterologous, i.e., foreign, to the transgenic plant or cell into which it is introduced, or, is homologous to an endogenous gene of the transgenic plant or cell into which it is introduced, but which is designed to be inserted, or is inserted, into the plant's genome in Such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene. As used herein, a "transgenic plant" is any plant in which one or more, or all, of the cells of the plant includes a transgene. The transgene can be introduced into the cell, directly or indirectly by introduction into a precursor of the cell, by way of deliberate genetic manipulation, such as by T-DNA mediated transfer, electroporation, or protoplast transformation. The transgene may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as a leaf, a root, or a stem.

As used herein, the term "hybridizes under stringent conditions" refers to conditions for hybridization in 6× sodium chloride/sodium citrate (SSC) at about 45° C., followed by one or more washes in 0.2×SSC, 0.1% SDS at 50–65° C.

A "heterologous promoter", when operably linked to a nucleic acid sequence, refers to a promoter which is not naturally associated with the nucleic acid sequence.

As used herein, an agent with "insecticidal activity" is an agent which when tested by the following assay has measurable insect-killing activity. In the assay, the agent is combined with mung bean flour produced from an insect-sensitive mung bean strain and packed as an artificial bean. Insect eggs are placed on the artificial bean. The timing and number of hatched insects are measured. An agent with "insecticidal activity" demonstrates delayed hatched, e.g., a delay of about 2, 4, 5, 7, 10, or 14 days. Alternatively, the agent can prevent hatching, e.g., only about 80%, 60%, 40%, 30%, 10%, or 0% of the eggs hatch after 14 days.

As used herein, an agent with "fungicidal activity" is an agent which when tested in the following assay produces a measurable zone of growth inhibition. The agent, in an acceptable solvent, is soaked in a sterile filter disc which is placed on an agar plate top spread with a fungus, e.g., *Rhizoctonia solani*. The plates are incubated, e.g., for 36–48 hours, and then zone of growth inhibition around each filter disc is measured. An agent with "anti-fungal activity" produces a zone of inhibition of about 1, 2, 3, 4, 5 mm or greater after 36 hours of fungus growth.

As used herein, an agent which "inhibits messenger RNA translation in a wheat germ extract" is an agent which when present in an in vitro translation reaction obtained by combining a messenger RNA with a wheat germ extract, e.g., a commercial wheat germ extract, prevents incorporation of [$^{35}$S] methionine into an acid insoluble fraction by at least 30%, e.g., at least about, 50%, 75%, or 100%

The discovery of a polypeptide thionin from insect resistant mung beans with insecticidal properties and its encoding nucleic acid sequence has a variety of commercial and agriculture benefits. The polypeptide can be used in a composition, e.g., a composition which includes agriculturally acceptable carriers, or other agents, to protect plants from insects, and other pests and pathogens. The composition can be formulated and applied by methods described herein in order to protect a plant. In another aspect, the nucleic acid can be used to generate a transgenic plant which expresses the thionin to thereby protect the plant. By conferring resistance to damage by insects, these strategies are of considerable economic benefit.

Other features, objects, and advantages of the invention will be apparent from the description and from the claims.

DETAILED DESCRIPTION

The invention provides nucleic acids and polypeptides with insecticidal properties. These molecules can be isolated from a bruchid resistant line of the mung bean *Vigna radiata*. Moreover, isolated nucleic acids and isolated polypeptides of the invention can be used to provide pest and pathogen resistance in a variety of scenarios.

Assaying Resistance

A simple bioassay is utilized in order to assess the insecticidal properties of the plant lines, nucleic acids, and polypeptides featured herein. Bruchids, (e.g., bruchids obtained from the Asian Vegetable Research and Development Center (AVRDC), P.O. Box 42, Shanhua, Tainan 741, Taiwan, are maintained on sensitive mung bean seeds, e.g., on VC1973A seeds. To assay mung bean plants for resistance, seeds are obtained from the plant in question. Six bruchid eggs are placed on a seed. Multiple seeds from a single plant in question can be so tested. The seeds are incubated at 25° C. and 60% humidity, and observed daily. The number of live bruchids emerging each day is monitored, and compared to data obtained from control sensitive and resistant lines.

In order to determine if a composition, e.g., a formulation containing a polypeptide featured in this invention, has insecticidal properties, the above bioassay is easily adapted to testing the composition. Flour is produced from sensitive mung beau seeds, combined with the composition and molded into an artificial seed following the method of Shade et al.(1986) *Bio/Technology* 12:793–796. Again, six bruchid eggs are placed on each seed. The artificial seeds are monitored as the real seeds described above.

Polypeptide Expression

The nucleic acids featured herein can be utilized to express polypeptides with insecticidal properties. Methods for expressing and obtaining polypeptides from coding nucleic acids sequences are routine in the art. The coding nucleic acid sequence for mung bean thionin can be cloned into an expression vector, for example, a bacterial expression vector. The vector can have an inducible promoter, e.g., the lac promoter or a derivative thereof. Alternatively, the vector can have a T7 polymerase promoter. The vector can also include nucleic acid sequences encoding a polypeptide tag or fusion gene to facilitate purification of an inserted heterologous coding sequence. For example, the tag can be a short peptide epitope for an antibody, or a purification handle such as hexa-histidinie. The tag can encode a completely folded polypeptide, such as glutathione-S-transferase, maltose binding protein, or chitin binding domain. Between the tag and the inserted coding sequence can be sequence encoding a site specific protease recognition site. The vector can include a sequence to export the desired polypeptide into the periplasm.

The vector is transformed into a host cell, e.g., *E. coli* DH5α. Transformed cells can be propagated, and treated with an inducer to activate polypeptide expression.

If the expressed polypeptide is fused to a tag or fusion gene with a purification handle, the polypeptide can be easily purified from a clarified cell lysate with an appropriate affinity column, e.g., $Ni^{2+}$ NTA resin for hexa-histidine, glutathione agarose for GST, amylose resin for maltose binding protein, chitin resin for chitin binding domain, and antibody affinity columns for epitope tagged proteins. Tile desired polypeptide can be eluted form the affinity column, or if appropriate cleaved from the column with a site specific protease. If the protein is not tagged for purification, routine methods in the art can be used to develop procedures to isolate it from cell lysates, periplasm, or the media (see, e.g., Scopes, R K (1994) *Protein Purification: Principles and Practice*, 3rd ed., New York: Springer-Verlag).

Analogs of mung bean thionin include thionins (or biologically active fragments thereof) whose sequences differ from the wild-type sequence by one or more conservative amino acid substitutions or by one or more non-conservative amino acid substitutions, deletions, or insertions which do not abolish bruchid killing activity. The following table list suitable amino acid substitutions:

TABLE 1

CONSERVATIVE AMINO ACID REPLACEMENTS

| For Amino Acid | Code | Replace with any of |
| --- | --- | --- |
| Alanine | A | Gly, Ala, Cys |
| Arginine | R | Lys, Met, Ile, |
| Asparagine | N | Asp, Glu, Gln, |
| Aspartic Acid | D | Asn, Glu, Gln |
| Cysteine | C | Met, Thr |
| Glutamine | Q | Asn, Glu, Asp |
| Glutamic Acid | E | Asp, Asn, Gln |
| Glycine | G | Ala, Pro, |
| Isoleucine | I | Val, Leu, Met |
| Leucine | L | Val, Leu, Met |
| Lysine | K | Arg, Met, Ile |
| Methionine | M | Ile, Leu, Val |
| Phenylalanine | F | Tyr, His, Trp |
| Proline | P | |
| Serine | S | Thr, Met, Cys |
| Threonine | T | Ser, Met, Val |
| Tyrosine | Y | Phe, His |
| Valine | V | Leu, Ile, Met |

Promoters

For polypeptides which confer resistance to pests or pathogens, the isolated coding nucleic acid sequence can be operably linked to a heterologous promoter. The promoter can activate transcription and, thus, polypeptide expression in a subset of tissues. Alternatively, the promoter can alter transcription rates in response to environmental stimuli, systemic signals, or intracellular signals. For example, promoters are known which respond to excessive heat, tissue injury, pathogen infection, or cell wounding, e.g., wounding due to pest attack. Known signals for promoters included methyl jasmoonate, absiscic acid, gibberillins, salicylic acid, ethylene, $HgCl_2$, and $H_2O_2$. Methyl jasmonate responsive promoters include vspB (Mason et al. (1993) *Plant Cell* 5:241–251), and the tomato HMG2 promoter (U.S. Pat. No. 5,689,056). An example of a gibberillin response promoter is the Amy1/6-4 promoter of rice (Skriver et al. (1991) *Proc. Natl. Acad. Sci. USA* 88:7266–7270). Promoters which respond to pathogen infection include the grape stilbene synthase promoter (U.S. Pat. No. 6,072,103). Promoters which respond to cell wounding include the win1 and win2 promoters (Weiss and Bevan (1991) *Plant Physiol.* 96:943–951), and the PinII promoter (U.S. Pat. No. 5,684, 239). For example, any of these promoters can be operably linked to a nucleic acid sequence of SEQ ID NO:1 in order to regulate expression of the polypeptide of SEQ ID NO:2. Similarly, any of these promoters can be operably linked to variants or fragments of SEQ ID NO:1, or other similar coding nucleic acid sequences.

Methods of Transforming Plant Cells

A nucleic acid construct of the present invention can be transformed into a plant cell to produce a desired transgenic plant or plant cell. Methods for transforming plant cells with nucleic acid are routine in the art. Further, the plant cells can be transformed with multiple constructs, e.g., sequentially or concurrently. Depending on the desired physiological and agronomic properties of a plant species, and the nucleic acid construct of the present invention, a target plant or plant cell for transformation can include a species from maize, wheat, rice, soybean, tomato, tobacco, carrots, peanut, potato, sugar beets, sunflower, yam, Arabidopsis, rape seed, sunflower, and petunia.

One implementation of the current invention utilizes *Agrobacterium*, to introduce the desired construct into plant cells such as in U.S. Pat. Nos. 5,177,010, 5,104,310, 5,149, 645, 5,469,976, 5,464,763, 4,940,838, 4,693,976, 5,591,616, 5,231,019, 5,463,174, 4,762,785, 5,004,863, and 5,159,135; and European Patent Applications 11 6718, 290799, 320500, 604662, 627752, 0267159, and 0292435). The method can be used with both dicotyledonous plants cells (Bevan et al. (1982) *Ann. Rev. Genet.* 16:357–384; Rogers et al. (1986) *Methods Enzymol.* 118:627–641), and monocotyledonous plant cells. (Hernalsteen et al. (1984) *EMBO J* 3:3039–3041; Hooykass-Van Slogteren et al. (1984) *Nature* 311:763–764; Grimsley et al. (1987) *Nature* 325:1677–179; Boulton et al. (1989) *Plant Mol. Biol.* 12:31–40.; Gould et al. (1991) *Plant Physiol.* 95:426–434). The method employs binary *Agrobacterium* T-DNA vectors (Hoekema et al. (1983) *Nature* 03:179; Bevan, 1984, *Nuc. Acid Res.* 12:8711–8721), and the co-cultivation procedure (Horsch et al., 1985, *Science* 227:1229–1231).

Additional steps may be required to prepare a desired nucleic acid sequence for plant transformation. For example, in order to utilize T-DNA mediated transformation, the thionin coding sequence, operably linked to a heterologotus promoter, is ligated into a binary vector, between the left and right border sequences of T-DNA. The binary vector further includes an Hph gene coding for hygromycin resistance. The binary vector containing the desired construction is transformed into an *E. coli* strain, e.g., DH5α. Subsequently, the binary plasmid is transferred into an *Agrobacterium*, e.g., *Agrobacterium* strain LBA4404, using a tri-parental mating.

Meanwhile, plants are prepared to receive the T-DNA with the transgene. Leaf discs are obtained from axenically grown tobacco seedlings. The discs are incubated for 8 hours on sterile filter papers overlaid on tobacco nurses cells on a feeder plate containing modified MS medium with Nitsch vitamins, 100 ml/L myo-inositol, 30 mg/L sucrose, 0.4 mg/L BAP, 1 mg/L 2,4-D (dichlorophenoxyacetic acid), 8 ml/L agar. To establish co-cultivation, the filters bearing the leaf disks are submersed in a suspension of the *Agrobacterium* bearing the desired binary vector, the bacteria being a concentration of approximately $1 \cdot 10^9$ cell/ml, and vacuum infiltrated (3×1 minute). The filters and leaf discs are incubated on the nurse plate for 48 hours at 25° C. with indirect light. Then the discs are transferred to selection/regeneration plates containing MS salts, Nitsch vitamins, 100 ml/L myo-inositol, 20 g/L sucrose, 2 mg/L zeatin, 4 g/L agar, 500 μg/ml carbemicillin and an appropriate antibiotic, e.g., G418 to select for the hygromycin resistance gene. The plates are placed in a growth chamber at 25° C. for 18 hours with light. The resulting shoots were transferred to rooting media, grown into plantlets, transferred to soil, and grown into plants in a green hose. One skilled in the art can adapt this method to transform other species of plants.

Other methods for transforming plant cells are available. Of particular utility for transforming monocotyledonous plants or plant cells are methods of protoplast transformation which include, but are not limited to, protoplast transformation through calcium-, polyethylene glycol (PEG)- or electroporation-mediated uptake of naked DNA (see Paszkowski et al., 1984, *EMBO J* 3:2717–2722, Potrykus et al. 1985, *Molec. Gen. Genet.* 199:169–177; Fromm et al., 1985, Proc. Nat. Acad. Sci. USA 82:5824–5828; Shimamoto, 1989, *Nature* 338:274–276), microinjection, silicon carbide mediated DNA uptake (Kaeppler et al., 1990, *Plant Cell Reporter* 9:415–418), and microprojectile bombardment (see Klein et al., 1988, *Proc. Nat. Acad. Sci. USA* 85:4305–4309; Gordon-Kamm et al., 1990, *Plant Cell* 2:603–618), whiskers technology (see U.S. Pat. Nos. 5,302,523 and 5,464,765), and viral vector systems (see, U.S. Pat. Nos. 5,316,931, 5,589, 367, 5,811,653, and 5,866,785).

A transformed plant or transformed plant tissue can be assayed for resistance to pathogens, insects, and other pests (e.g., by a field trial or by a method described herein).

Agricultural Compositions

Polypeptides, e.g., mung bean thionin protein, can be formulated as a composition which is applied to plants in order to confer insect, pest, or pathogen resistance. The composition can be prepared in a solution, e.g., an aqueous solution, at a concentration from about 0.005% to 10%, or about 0.01% to 1%, or about 0.1% to 0.5% by weight of polypeptide content. The solution can comprise an organic solvent, e.g., glycerol or ethanol. Alternatively, the composition can be formulated with one or more agriculturally acceptable carriers. Agricultural carriers can include: clay, talc, bentonite, diatomaceous earth, kaolin, silica, benzene, xylene, toluene, kerosene, N-methylpyrrolidone, alcohols (methanol, ethanol, isopropanol, n-butanol, ethylene glycol, propylene glycol, and the like), and ketones (acetone, methylethyl ketone, cyclohexanone, and the like). The formulation can optionally further include a stabilizer, spreading agent, wetting extenders, dispersing agents, sticking agents, disintegrators, and other additives, and can be prepared as a liquid, a water-soluble solid (e.g., tablet, powder or granule), or a paste.

Prior to application, the solution can be combined with another desired composition such a insecticide, germicide, fertilizer, plant growth regulator and the like. The solution may be applied to the plant tissue, for example, by spraying, e.g., with an atomizer, by drenching, by pasting, or by manual application, e.g., with a sponge. The solution can also be distributed from an airborne source, e.g., an aircraft or other aerial object, e.g., a fixture mounted with an apparatus for spraying the solution, the fixture being of sufficient height to distribute the solution to the desired plant tissues. Alternatively, the composition can be applied to plant tissue from a volatile or airborne source. The source is placed in the vicinity of the plant tissue and the composition is dispersed by diffusion through the atmosphere. The source and the plant tissue to be contacted can be enclosed in an incubator, growth chamber, or greenhouse, or can be in sufficient proximity that they can outdoors.

In another implementation, if the composition is distributed systemically thorough the plant, the composition can be applied to tissues other than the leaves, e.g., to the stems or roots. Thus, the composition can be distributed by irrigation. The composition can also be injected directly into roots or stems.

Without further elaboration, it is believed that the above description has adequately enabled the present invention. The following examples are, therefore to be construed as merely illustrative, and not limitative of the remainder of the disclosure in any way whatsoever. All of the publications cited herein are hereby incorporated by reference in their entirety.

Materials and Methods

Plant and Insect Materials

Two nearly isogenic lines of mung bean *Vigna radiata* L. VC 1973A and VC6089A were obtained from the Asian Vegetable Research and Development Center (AVRDC). VC6089A ($BC_6S_2$) populations were crossed to wild mung bean *Vigna radiata* TC1966 as donor parent and breeding line VC1973A as recurrent parent. Azuki bean weevil *Callosobruchus chinensis* (L.) was also obtained from AVRDC that has been maintained on VC1973A at 25° C. in a growth chamber.

Isolations and Analyses of RNA and DNA

Total RNA was isolated via a modified hot phenol extraction method (Verwoerd et al. (1989) *Nucl Acids Res* 17:2362). Polyadenylated RNA was prepared by Oligo(dT)-cellulose affinity column (Maniatis et al. (1982) *Molecular Cloning: A Laboratory Manual* Cold Spring Harbor Laboratory Press, Cold Spring Harbor, N.Y.). RNA concentration was determined by measuring its absorbance at 260 nm and verified by agarose gel electrophoresis and ethidium bromide staining. To confirm equal loading of total RNA on RNA gel blots, a 0.2 kb fragment of VrCRP was PCR amplified and used as a probe. Genomic DNA isolation was performed via a modified CTAB extraction method (Dellaporta et al. (1983) *Plant Mo. Biol. Rep.* 1:19). DNA gel blot analysis, including restriction, fragment length polymorphism, and downward alkaline capillary transfer to a positively charged nylon membrane (Hybond N+, Amersham Pharmacia Biotech, Baue D'Urfe, Canada) were performed as described by Young et al. ((1992) *Theor. Appl. Genet.* 84:839–844) and Chomczynski ((1992) *Anal. Biochem.* 201:134–139). Hybridization of the membrane was performed under high-stringency condition at 65° C. overnight, and after hybridization the membrane was washed twice with 2×SSC/1% SDS for 15 min at room temperature, and then washed twice with 0.2×SSC/1% SDS at 55° C. for 15 min (1×SSC is 0.15M NaCl, 0.015 M sodium citrate, pH 7.0). RNA gel blot analyses were also carried out as described by Chomczynski (1992) supra. RNAs were downward alkaline capillary-transferred onto Hybond N+ nylon membranes and cross-linked with a Stratalinker™ UV Crosslinker 1800. Hybridization and washing of the membranes was performed as described previously. Probes for both DNA and RNA gel blot analysis were synthesized from random-labeled isolated DNA inserts with $\alpha$-$^{32}$P-dCTP. The membranes were exposed to phosphorimager, and scanned.

Suppression Subtractive Hybridization

Suppression subtractive hybridization (SSH) was performed on VC6089A cDNA and matched VC1973A cDNA, using the PCR select cDNA subtraction kit (Clontech Laboratories Inc., CA) according to the manufacturer's recommendations. VC6089A and VC1973A seeds were collected 15 DAF (days after flowering). mRNA was prepared from the seeds as described above, and reverse transcribed to generate cDNA, which is then converted to double-stranded DNA. The two cDNA populations were subtracted as described (Akopyants et al., ((1998) *Proc. Natl. Acad. Sci. USA* 95: 13108–13113). Briefly, the VC6089A cDNA, designated the "tester DNA", was digested with a restriction enzyme, e.g., AluI, and divided into two pools. Each pool was ligated to a different linker adaptor. The VC1973A DNA was used as the "driver DNA," and was restricted with the same enzyme. Each pool of VC6089A cDNA was denatured and hybridized to an excess of digested driver DNA. Subsequently, the mixtures were cooled, and the DNA ends were extended in order to incorporate the adaptor end into the driver DNA strand. Finally, the two pools were combined, denatured, and reannealed. The ends of the reannealed strands were filled in with DNA polymerase. PCR amplification was used to amplify fragments that had two different linkers at each end, one from each pool. The procedure highly favors amplification of DNAs which were unable to anneal to DNA in the driver DNA population, i.e., cDNAs were are more abundant in VC6089A seeds than VC1973A seeds.

The amplified DNAs were cloned into the pGEM-T vector, transformed into competent *E. coli* cells, and grown in 96-well dishes. Each clone was transferred to a nitrocellulose membrane for blot hybridization to identify vectors with inserts. Inserts were amplified by PCR using the universal primers T7 and SP6, sequenced, and used for Northern blot analysis against mRNA from sensitive (VC1973A) and resistant (VC6089A) seeds. One DNA fragments which was differentially expressed in VC6089A contains nucleic acid encoding VrCRP.

Sequencing of DNAs and Peptides

DNA sequencing was carried out using a ABI autosequencer 377. N-terminal amino acid sequences were determined by automatic Edman degradation method using a gas-phase protein sequencer (Applied Biosystems, Model 473A). After SDS-PAGE separation, polypeptides were electroblotted onto a PVDF membrane and detected by Coomassie blue staining. Bands corresponding to the desired polypeptides were cut and processed for amino acid sequencing.

Construction of an Expression Vector

Two degenerate oligonucleotides were synthesized: VrCRF (5'-CAT GCC ATG GAG AGA GGA GAG GCT AGA AC-3') (SEQ ID NO:5) and VrCRR (5'-TCC CCC GGG ACA GTT GAC GAG GCA ATA-3') (SEQ ID NO:6). VrCRF corresponds to the degenerate codons of the amino acids Glu$^{23}$ to Arg$^{28}$ (N-terminal amino acid methionine of the signal peptide is numbered as amino acid 1) of VrCRP and has a sense orientation and a NcoI site. VrCRR corresponds to the degenerate codons of the amino acids Tyr$^{68}$ to Cys⁷³ of VrCRP and has an antisense orientation and a SmaI site. PCR was performed essentially by the method of DNA polymerase chain reaction (Saiki et al., 1988), using 5 ng of VrCRP as target DNA, 10 pmol each of VrCRR and VrCRF, 250 nmol each of the dNTPs and 2.5 U Taq polymerase (Promega) in a total volume of 100 µL. The amplification program included an initial step at 95° C. for 5 min, 25 cycles (95° C. for 1 min, 55° C. for 1 min, and 72° C. for 1 min) and a final step at 72° C. for 10 min. The 171 bp amplification product was purified on a 1% agarose (FMC BioProducts) gel and excised from the gel with a razor blade (Chuang et al. (1994) *Biotechniques* 17:634–636). The sequence of the amplification product was confirmed by DNA sequencing. The amplification product and pTYB4 expression vector that has NcoI and SmaI sites on its multiple cloning sites (New England Biolabs, MA) were digested with NcoI and SmaI. The two restriction endonuclease-digested mixtures were combined and ligated with T4 DNA ligase (Promega). The nucleotide sequence of the insert in the construct was verified by DNA sequencing.

Expression and Purification of VrCRPΔsp

A nucleic acid sequence (including SEQ ID NO:3) encoding a signal peptide truncated form of VrCRP, denoted as VrCRPΔsp (SEQ ID NO:4 and an N-terminal methionine, and two C-terminal junction residues) was cloned into the pTYB4 expression vector which contains a heterologous bacterial T7 promoter. The resulting construct, pTYB4-VrCRPΔsp, was transferred to *E. coli* BL21(DE3). The *E. coli* transformants were cultured in LB (Luria Bertani) liquid medium containing 100 µg mL⁻¹ ampicillin at 37° C. overnight. The overnight culture was diluted to 50-folds with LBA broth and cultured at 37° C. for about 2 h ($A_{600}$=0.3 to 0.4). Then culture was gently shaken in an ice bath to bring the temperature down to 24° C. and allowed to grow at 24° C. thereafter. IPTG was added to the culture at a final concentration of 0.3 mM and the culture was incubated at 24° C. for 6 h. The culture was then put into an ice bath for 30 min and the *E. coli* cells were harvested by centrifugation at 4° C., 4400×g for 15 min. The expressed VrCRP was purified by intein mediated purification system with an affinity chitin-binding tag according to the method previously described (Chonig et al., 1997, *Gene* 192:271–281). The cells were washed once with distilled water and suspended in a lysis buffer (20 mM Tris-HCl pH 8.0, 500 mM NaCl, 0.1 mM EDTA, 0.1%, Triton X-100, 0.1% TWEEN-20) to obtain a cell suspension ($A_{600}$=25 to 30). The cell suspension was homogenized with Microfludizer and cell debris were removed by centrifugation at 12,000×g for 10 min. The supernatant was filtered through a 0.45 µm membrane filter. The filtrate containing VrCRP-chitin binding domain (CBD) fusion protein was passed through a chitin affinity column (16×100 mm, bed volume: 30 mL) at a flow rate of 0.4 mL min⁻¹. The column was washed with 15–20 fold bed volume of a washing buffer (20 mM Tris-HCl pH 8.0, 500 mM NaCl, 0.1 mM EDTA, 0.1% Triton X-100, 0.1% TWEEN-20) at a flow rate of 0.9 mL min⁻¹. The VrCRPΔsp-CBD fusion protein bound to the affinity column was cleaved with DTT by introducing 2.5 fold bed volume of a cleavage buffer (20 mM Tris-HCl pH 8.0, 50 mM NaCl, 0.1 mM EDTA, 30 mM DTT) into the column. The column was then saturated with the cleavage buffer and kept at 4° C. for 16 h. VrCRPΔsp was eluted from the column with an elution buffer (20 mM Tris-HCl pH 8.0, 50 mM NaCl, 0.1 mM EDTA). VrCRPΔsp was further purified with FPLC system using Superdex peptide HR 10/30 column (10× 300–310 mm, bed volume 24 mL) (Pharmacia) to remove small amounts of contaminating proteins. The column was equilibrated with 20 mM Tris-HCl pH 8.0, 50 mM NaCl, 0.1 mM EDTA, 10 mM β-mercaptoethanol and VrCRPΔsp was eluted with the same buffer at a flow rate of 1.0 mL min⁻¹. The purified VrCRPΔsp was homogeneous as examined by SDS-PAGE.

Bioassay of VrCRPΔsp Activity

Activity of VrCRPΔsp against *C. chinensis*, one of the major bruchid pests of mung bean, was studied with artificial mung bean seeds. The artificial seeds were prepared according to the method of Shade et al.((1986) *Bio/Technology* 12:793–796) with modification. The artificial seeds have an average volume and weight of 95 μL and 98.6 mg, respectively. Each seed is sufficient to hatch six eggs of *C. chinensis*. Thirty artificial seeds were divided into 6 groups for a six-replicate experiment. Ten pairs of *C. chinensis* with equal number of male and female bruchids were introduced into the growth chamber and allowed to lay eggs on the seeds for 24 hours. The number of eggs on the surface of each seed was strictly controlled to six by destroying the extra eggs with a small needle. The seeds were incubated at 25° C. and 60% relative humidity and examined for within-seed development times (WSDT) and percentage emergence at proper time interval. The results were subject to statistic analysis using unpaired student t-test.

Effect of VrCRPΔsp on the Growth of *Spodoptera frugiperda* Cells

Fall armyworm (*Spodoptera frugiperda*, Sf 21, Gibco) cells were grown in TNM-FH medium (TNM-FH insect medium, Sigma, T1032) that contained 8% fetal bovine serum (FBS) at 28° C. for 3 days. The cell number was counted under microscope and adjusted to $6\times10^5$ cells per unit. Appropriate amounts of VrCRPΔsp were added and cultured for 3 days. The number of cells was counted under microscope.

In Vitro Translation Inhibition Assay

The reaction mixture contained 0.75 μL potassium acetate (1 M), 0.5 μL BMV (Brome Mosaic Virus) RNA (Promega Co.) (0.5 μg $\mu L^{-1}$), 2 μL unlabeled amino acid mixture except methionine, 1 mM, 1.9 μL L-[$^{35}$]methionine (500 μCi, Amersham, AG1094), 12.5 μL wheat germ extract (Promega, L4380), 0.5 μL Rnasin (40 U $\mu L^{-1}$) and 10 to 40 [M VrCRPΔsp. The final volume was adjusted to 25 μL by nuclease-free water. The reaction mixture was incubated at 25° C. for 90 min. Aliquots of the reaction mixture were taken, spotted on to a glass-fiber filter and dried at 45° C. for 3 minutes. The filters were dipped in 10% trichloroacetic acid (TCA) then washed thoroughly with 5% TCA, and then finally washed with 95% ethanol and dried. Radioactivity was measured in a liquid scintillation counter.

Preparation of Antiserum

Two New Zealand white rabbits were used for raising antibodies against the purified VrCRPΔsp. The purified VrCRPΔsp was covalently coupled to keyhole limpet hemocyanin (KLH) using the bifunctional reagent glutaraldehyde and mixed with complete adjuvant (TiterMax Antiserum Preparation Gold). The rabbits were injected with the antigen-KLH-adjuvant mixture 3 times with a 4-week interval between injections. The amounts of VrCRPΔsp used for the injections were 150, 100 and 50 μg for the first, second and third injection, respectively. The rabbits were bled from carotid artery one month after the final injection. The blood clot was centrifuged for 10 min at 400×g at 4° C. The clear serum was removed and the complement system was inactivated by incubating at 56° C. for 30 min. The serum was lyophilized and stored at −70° C.

Western Blot Analysis

Proteins were resolved with 12.5% SDS-PAGE and transblotted to a PVDF (Polyvinylidene fluoride) membrane using capillary transfer (Zeng et al., 1999, *Biotechniques* 26:426–430). The membrane was washed with TBST (10 mM Tris-HCl pH 8.0, 150 mM NaCl, 0.05% TWEEN-20) and equilibrated with TBST containing 1% bovine serum albumin. The blot on the membrane was treated with anti-VrCRPΔsp antiserum for 90 min and washed. Then treated with the second antibody (anti-rabbit IgG, AP-linked) for another 90 mml. After washing the membrane was incubated with the coloring reagent 5-bromo-4-chloror-3-indolylphosphate/nitro blue tetrazolium (BCIP/NBT) at 25° C. for 4 min. The reaction was terminated by washing the membrane with distill water for 10 min.

RESULTS

Isolation of VrCRP cDNA

Plant lines which exhibit resistance to pests and pathogens, e.g., to bruchids, are a valuable source for the identification of factors which can confer pest and pathogen resistance. Such plants can be bred to another line of the same species, which is sensitive to the pest. Mendelian analysis of the progeny indicates of the number of heterogeneous genes contributing to resistance. Resistant progeny are identified, e.g., by the bruchid resistance assay described below, and repeatedly bred to create a resistant plant line, nearly isogenic to the sensitive plant line. Thus, one can produce two nearly isogenic lines of the mung bean *Vigna radiata*, such as VC1973A and VC6089A. It was known that VC1973A seeds are susceptible to bruchid *Callosobruchus chinensis*, whereas VC6089A seeds are resistant to bruchids. Feeding tests of *C. chinensis* on the seeds of VC1973A and VC6089A revealed that the developing seeds of VC6089A were bruchid resistant around 15 days after flowering (DAF). The two lines of *Vigna radiata* L. VC1973A and VC6089A were obtained from Asian Vegetable Research and Development Center, P.O. Box 42, Shanhua, Tainan 741, Taiwan.

Subsequently, a variety of methods can be used to identify pest-resistant genes. For example, the resistant gene locus can be genetically mapped to a chromosomal locus. Nucleic acid can be isolated from the locus by a variety of techniques, including the use of markers, walking techniques, genomic libraries, and the polymerase chain reaction.

Alternatively, differential gene expression analysis techniques can be used to identify the resistant alleles. A tissue is identified which exhibits resistance to the pest. mRNA is isolated from the same tissue from isogenic or nearly isogenic, resistant and sensitive plants, and reverse transcribed. The cDNA population unique to the resistant tissue is identified by subtractive hybridization techniques, which are routine for skilled artisans. After subtraction, cDNAs which are expressed in the resistant, but not the sensitive strain are available for amplification, cloning, and sequencing.

By using suppression subtractive hybridization a full-length cDNA, named VrCRP, was isolated from the bruchid resistant line *Vigna radiata* L. VC6089A. This cDNA (SEQ ID NO:1) encodes a protein of 73 amino acids containing 8 cysteine residues and a signal peptide of 22 amino acids. The sequence of the encoded protein is recited in SEQ ID NO:2. The VrCRP has a cysteine stabilized α-helix motif(CSH motif) similar to a number of cysteine-rich proteins (Kobayashi et al., 1991, *Biopolymer* 31:1213–1220; Froy et al., 1998, *FASEB J* 12:1793–1796) and shows amino acid sequence homology to fabatin-1 and fabatin-2 isolated from *fava* bean (*Vicia faba*) (47.6%. identity) (Zhang et al., 1997, *FEMS Microbiol. Lett.* 149:59–64), α-amylase inhibitor from *sorghum* (*Sorghum bicolor*) (42.6% identity) (Bloch et al., 1991, *FEBS Lett.* 279:101–104) and weak homology (less than 40%) to a number of other small cysteine-rich proteins from a variety of organisms. The VrCRP protein also contains a signal sequence. A variant of the VrCRP protein lacking the signal sequence is designated as VrCRPΔsp, and consists of 51 amino acids of VrCRP, commencing with the $23^{rd}$ residue of VrCRP, and terminating at the final residue of VrCRP. This variant has an additional methionine at its N-terminus, and a proline and glycine at its C-terminus.

Expression of VrCRP in *E. coli*

*E. coli* M15 transformed with pQE30 harboring full-length VrCRP failed to express VrCRP. The transformants lysed after the IPTG induction (isopropyl β-D-thiogalactopyranoside). When *E. coli* M15 cells were induced at $A_{600}$=~0.3 to 0.5, cell growth was arrested within one hour. Electron microscopic analysis revealed gross morphological aberrations in the induced cells relative to induced cells lacking VrCRP plasmid. The results indicate that VrCRP is toxic to *E. coli* M15. *E. coli* harboring signal peptide truncated VrCRP (denoted as VrCRPΔsp) grow normally at an early stage similar to control *E. coli* M15 cells, but their growth slowed down after 1 hour, and stopped alter 2 hours. On the other hand, *E. coli* transformants harboring VrCRP failed to grow to an even greater extent.

Expression was improved by using signal peptide deleted VrCRP in an IMPACT (intein mediated purification with an affinity chitin-binding tag, New England Biolabs, MA) expression system. As described above, VrCRPΔsp is a 54 amino acid protein of which 51 amino acids are derived from VrCRP, while the three remaining (methionine, proline, and glycine) are terminal residues resulting from the cloning vector. The system IMPACT was used to express signal peptide truncated VrCRP. The expressed VrCRPΔsp fusion protein with a molecular mass of 60.9 kDa was bound to a chitin affinity column. The fusion protein was cleaved with DTT (1,4-dithiothreitol) to give rise to a VrCRPΔsp with a molecular mass of 5.9 kDa., and migrates as such on an 4–12% gradient SDS polyacrylamide gel (SDS-PAGE). The eluted VrCRPΔsp was further purified to apparent homogeneity by a Superdex Peptide HR 10/30 column, as determined by electrophoresing 4 μg of the purified protein oil a silver-nitrate stained SDS-PAGE gel. The purified VrCRPΔsp was characterized by its molecular mass (5.9 kDa) and N-terminal amino acid sequencing. The purified VrCRPΔsp showed molecular mass of 5.9 kDa in SDS-PAGE that corresponds to the calculated molecular weight 5.944 kDa. The forty amino acid N-terminal sequence of VrCRPΔsp completely matched to the corresponding nucleotide sequence of VrCRP.

Bruchid Resistant Activity of VrCRP

To determine whether VrCRPΔsp plays a role in bruchid resistance or not, artificial seeds containing different amounts (0.01%–0.25%, w/w) of the purified VrCRPΔsp were produced. The seeds were tested for this resistance to *C. chinensis*. Intact mung bean seeds (TN5, VC1973A and VC6089A) and artificial seeds made from the flour of these three mung bean varieties were also tested for comparison. Bruchids were allowed to lay eggs on the intact and artificial seeds. The number of eggs on the surface of each seed was confined to six by destroying the extra eggs. The seeds were incubated at 25° C. and 60% relative humidity. Within-seed development times (WSDT) and percentage emergence are used as criteria for bruchid resistance. The results are shown in Table 1:

TABLE 1

| Material Screened | Within seed development time | Percentage Emergence |
|---|---|---|
| Intact Seeds | | |
| TN5 | 26.3 ± 0.6 | 100 ± 0 |
| VC1973A | 25.9 ± 0.9 | 100 ± 0 |
| VC6089A | — | 0 ± 0 |
| Artificial Seeds with from: | | |
| TN5 | 35.4 ± 1.6 | 51.3 ± 9.8 |
| VC1973A | 36.4 ± 1.6 | 53.1 ± 5.0 |
| VC6089A | — | 0 ± 0 |
| Artificial Seeds with purified protein: | | |
| VC1973A + 0.01% VrCRPΔsp | 40.7 ± 2.1 | 12.5 ± 5.9 |
| VC1973A + 0.09% VrCRPΔsP | 48 | 2.1 ± 5.9 |
| VC1973A + 0.20% VrCRPΔsp | — | 0 ± 0 |
| VC1973A + 0.25% VrCRPΔsp | — | 0 ± 0 |
| VC1973A + 0.25% BSA | 41.0 ± 2.6 | 52.6 ± 7.9 |

In intact seeds of susceptible mung beans, TN5 and VC1973A, 100% of the eggs hatched to produce adult bruchids after approximately 26 days. However, no adults emerged from eggs on intact VC6089A seeds, the bruchid resistant mung bean line.

Artificial seeds produced from flour from each respective mung bean line showed similar properties. In artificial seeds of susceptible mung beans, TN5 and VC1973A, greater than 50% of the eggs hatched to produced adult bruchids after approximately 35 days. Again, no adults emerged from artificial eggs made from intact VC6089A seeds, the bruchid resistant mung bean line.

Artificial seeds were used to test the efficacy of purified recombinant VrCRPΔsp. Artificial seed were produced with flour from the susceptible mung bean VC1973A combined with 0.01%, 0.09%, 0.20%, and 0.25% VrCRPΔsp. The seeds were compared to artificial seeds with 0.25% bovine serum albumin (BSA). The VrCRPΔsp at 0.01% concentration in the artificial seeds reduced the number of emerging bruchids to 12.5% compared to greater than 50% in the BSA control. Moreover, artificial seeds containing 0.2% VrCRPΔsp completely arrested bruchid development, as no adults emerged from such seeds. Artificial seeds with VrCRPΔsp at this concentration killed bruchid larvae at their first instar stage. Thus, a significant dosage response was observed between the VrCRPΔsp concentrations of 0.01%–0.2%. Thus purified recombinant VrCRPΔsp polypeptide is a potent antagonist of bruchid development and/or viability.

The performance of *C. chinensis* larvae reared on the artificial seeds containing various amounts (0.01%–0.25%) of VrCRPΔsp was also investigated. Six artificial seeds containing six eggs each were prepared for each dose. Two capsules containing six seeds each were opened after 21, 24, and 27 days respectively. The larvae were counted and weighted. The results were significant, e.g., P<0.035 for control compared to 0.01% VrCRPΔsp at 24 days, and P<0.001 for 0.01% VrCRPΔsp compared to 0.2% at 21 clays. Thus, artificial seeds containing 0.01% VrCRPΔsp significantly retarded larva development. Complete growth arrest was observed with seeds containing either 0.2% or 0.25% VrCRPΔsp (Table 2). These results provide additional evidence to support the toxicity of VrCRPΔsp to *C. chinensis*.

TABLE 2

Performance of *C. chinensis* larvae on artificial seeds containing VrCRPΔsp.

| | mean weight of larvae (mg) | | | |
|---|---|---|---|---|
| | Control (0%) | 0.01% VrCRPΔsp | 0.2% VrCRPΔsp | 0.25% VrCRPΔsp |
| Day 21 | 5.2 | 3.1 | 0 | 0 |
| Day 24 | 6.6 | 4.6 | 0 | 0 |
| Day 27 | 8 | 5.2 | 0 | 0 |

VrCRPΔsp Inhibits Protein Synthesis

The purified recombinant VrCRPΔsp polypeptide was combined with in vitro translation extracts to determine the effect of the polypeptide on translation. A 40 μM concentration of VrCRPΔsp protein completely inhibited the incorporation of amino acids including p355] methionine into acid insoluble fraction. A significant dosage response was observed between 10–40 μM of VrCRPΔsp. With 10 LM VrCRPΔsp, a greater than 60% reduction in acid insoluble counts was observed, with 40 μM, a greater than 80% reduction. The results indicated that VrCRPΔsp is a strong inhibitor of protein biosynthesis.

Effect of VrCRPΔsp on Growth of *Spodoptera frugiperda* Cells

VrCRPΔsp was added to the culture medium of an insect cell culture, a culture with cells of the fall armyworm (*Spodoptera frugiperda, Sf* 21). After VrCRPΔsp addition, cells were incubated at 28° C. and counted after three days. Purified VrCRPΔsp at 3.42 μM completely arrested the growth of Sf 21 cells. Rupture of Sf 21 cells under the conditions was observed by phase-contrast microscopy. The concentration of VrCRPΔsp that caused $LC_{50}$ (50% lethality concentration) was 1.7 μM.

Antifungal Activity of VrCRPΔsp

Sterile filter discs were prepared containing 0, 1, 2, 3, 6, 10, 20, and 40 μg of purified VrCRPΔsp in 20 mM TrisHCl pH 8.0, 50 mM NaCl, 0.1 mM EDTA. The filter discs were placed on agar plates which had been top spread with the fungus *Rhizoctonia solani*. The plates were incubated at 28° C. for 36 to 49 hours. The radius of the zone of inhibition was measured surrounding each disc. A zone of inhibition greater than 2 mm was observed for filter discs containing 10, 20, and 40 μg of purified VrCRPΔsp, indicating that at these concentrations, VrCRPΔsp has anti-fungal activity.

Additional Compositions

It was described previously that a single dominant bruchid resistance gene (Br) in the wild mung bean accession TC1966 has been transferred a susceptible cultivar and a resistant isogenic ($BC_{20}F_4$) line was developed by selection for bruchid resistance against the azuki bean weevil. Two novel cyclopeptide alkaloids, denoted vignatic acid A and B were identified in the resistant isogenic line. The addition of vignatic acid A to pellets of mung bean flour at concentrations more than 1% resulted in the complete elimination of the bruchids, but vignatic acid B had no observable effect on bruchids (Sugawara et al, 1996, *J. Agric. Food Chem.* 44:3360–3364; Kaga et al., 1998, *Mol. Gen. Genet.* 258: 378–384). However, the insecticidal activity of vignatic acid A alone was unable to explain the resistance of the resistant isogenic line to azuki bean weevil.

Other Embodiments are within the Following Claims.

What is claimed is:

1. A purified polypeptide comprising an amino acid sequence which is at least 80% identical to the amino acid sequence of SEQ ID NO:4, wherein the polypeptide has insecticidal or fungicidal activity.

2. The purified polypeptide of claim 1 wherein the polypeptide inhibits translation of a messenger RNA in a wheat germ extract.

3. A composition comprising the polypeptide of claim 1 present in an amount of 0.01% to 10% by weight of composition.

4. The composition of claim 3 wherein the polypeptide is present in an amount of 0.05% to 5% by weight of composition.

5. The polypeptide of claim 1 wherein the amino acid sequence is at least 90% identical to the amino acid sequence of SEQ ID NO:2.

6. The purified polypeptide of claim 5 wherein the polypeptide inhibits translation of a messenger RNA in a wheat germ extract.

7. A purified polypeptide comprising the amino acid sequence of SEQ ID NO:4.

8. A purified polypeptide comprising the amino acid sequence of SEQ ID NO:4, with up to 12 conservative amino acid substitutions, wherein the polypeptide has insecticidal or fungicidal activity.

9. A purified polypeptide encoded by a nucleic acid that hybridizes under high stringency conditions to a probe the sequence of which consists of the complement SEQ ID NO:1, wherein the polypeptide has insecticidal or fungicidal activity.

* * * * *

SEQUENCE LISTING

<160> NUMBER OF SEQ ID NOS: 6

<210> SEQ ID NO 1
<211> LENGTH: 326
<212> TYPE: DNA
<213> ORGANISM: Vigna radiata
<220> FEATURE:
<221> NAME/KEY: CDS
<222> LOCATION: (21)...(239)

<400> SEQUENCE: 1

```
acctcaacaa ttcatcactc atg gag aga aaa act ttc agc ttc ttg ttc tcg      53
                     Met Glu Arg Lys Thr Phe Ser Phe Leu Phe Ser
                      1               5                  10 ctc ctt ctc gtc tta gcc tct gat gtg gcc gta gag aga gga gag gct       101
Leu Leu Leu Val Leu Ala Ser Asp Val Ala Val Glu Arg Gly Glu Ala
             15                  20                  25 aga act tgt atg ata aag aaa gaa ggg tgg gga aaa tgc tta att gac       149
Arg Thr Cys Met Ile Lys Lys Glu Gly Trp Gly Lys Cys Leu Ile Asp
     30                  35                  40 acc acc tgt gca cat tcg tgc aag aac cgc ggt tac ata ggt gga gat       197
Thr Thr Cys Ala His Ser Cys Lys Asn Arg Gly Tyr Ile Gly Gly Asp
 45                  50                  55 tgc aaa ggc atg acg cgc acc tgc tat tgc ctc gtc aac tgt              239
Cys Lys Gly Met Thr Arg Thr Cys Tyr Cys Leu Val Asn Cys
 60                  65                  70 tgaacccttt tcgaatatca tatcatctta tcacaaataa atatagcagc atcactgcta    299
ctagtaccgc cctccgcacc acgccct                                         326
```

<210> SEQ ID NO 2
<211> LENGTH: 73
<212> TYPE: PRT
<213> ORGANISM: Vigna radiata

<400> SEQUENCE: 2

```
Met Glu Arg Lys Thr Phe Ser Phe Leu Phe Ser Leu Leu Leu Val Leu
 1               5                  10                  15

Ala Ser Asp Val Ala Val Glu Arg Gly Glu Ala Arg Thr Cys Met Ile
             20                  25                  30

Lys Lys Glu Gly Trp Gly Lys Cys Leu Ile Asp Thr Thr Cys Ala His
         35                  40                  45

Ser Cys Lys Asn Arg Gly Tyr Ile Gly Gly Asp Cys Lys Gly Met Thr
     50                  55                  60

Arg Thr Cys Tyr Cys Leu Val Asn Cys
 65                  70
```

<210> SEQ ID NO 3
<211> LENGTH: 156
<212> TYPE: DNA
<213> ORGANISM: Vigna radiata
<220> FEATURE:
<221> NAME/KEY: CDS
<222> LOCATION: (1)...(153)

<400> SEQUENCE: 3

```
gag aga gga gag gct aga act tgt atg ata aag aaa gaa ggg tgg gga       48
Glu Arg Gly Glu Ala Arg Thr Cys Met Ile Lys Lys Glu Gly Trp Gly
 1               5                  10                  15 aaa tgc tta att gac acc acc tgt gca cat tcg tgc aag aac cgc ggt       96
Lys Cys Leu Ile Asp Thr Thr Cys Ala His Ser Cys Lys Asn Arg Gly
```

-continued

```
                      20                  25                  30
tac ata ggt gga gat tgc aaa ggc atg acg cgc acc tgc tat tgc ctc      144
Tyr Ile Gly Gly Asp Cys Lys Gly Met Thr Arg Thr Cys Tyr Cys Leu
        35                  40                  45 gtc aac tgt tga                                                      156
Val Asn Cys
    50

<210> SEQ ID NO 4
<211> LENGTH: 51
<212> TYPE: PRT
<213> ORGANISM: Vigna radiata

<400> SEQUENCE: 4

Glu Arg Gly Glu Ala Arg Thr Cys Met Ile Lys Glu Gly Trp Gly
  1               5                  10                  15

Lys Cys Leu Ile Asp Thr Thr Cys Ala His Ser Cys Lys Asn Arg Gly
                20                  25                  30

Tyr Ile Gly Gly Asp Cys Lys Gly Met Thr Arg Thr Cys Tyr Cys Leu
        35                  40                  45

Val Asn Cys
    50

<210> SEQ ID NO 5
<211> LENGTH: 29
<212> TYPE: DNA
<213> ORGANISM: Artificial Sequence
<220> FEATURE:
<223> OTHER INFORMATION: Synthetically generated oligonucleotide

<400> SEQUENCE: 5
catgccatgg agagaggaga ggctagaac                                       29

<210> SEQ ID NO 6
<211> LENGTH: 27
<212> TYPE: DNA
<213> ORGANISM: Artificial Sequence
<220> FEATURE:
<223> OTHER INFORMATION: Synthetically generated oligonucleotide

<400> SEQUENCE: 6
tcccccggga cagttgacga ggcaata                                         27
```